US005376080A

United States Patent [19]

Petrussa

[11] Patent Number: 5,376,080
[45] Date of Patent: Dec. 27, 1994

[54] SINGLE USE RETRACTABLE NEEDLE SYRINGE

[76] Inventor: Gian L. Petrussa, Via Bixio 6, Udine, Italy, 33100

[21] Appl. No.: 918,857

[22] Filed: Jul. 27, 1992

[30] Foreign Application Priority Data

Jan. 30, 1991 [IT] Italy .................. UD91A000014
Jan. 24, 1992 [EP] European Pat. Off. ........ 92101146.6

[51] Int. Cl.⁵ .................. A61M 5/32; A61M 5/50
[52] U.S. Cl. .................. 604/198; 604/110
[58] Field of Search .................. 604/192–199, 604/263, 110, 164

[56] References Cited

U.S. PATENT DOCUMENTS

| 4,573,976 | 3/1986 | Sampson et al. | 604/198 |
| 4,863,435 | 9/1989 | Sturman et al. | 604/198 |
| 4,917,673 | 4/1990 | Coplin | 604/198 |
| 4,927,416 | 5/1990 | Tomkiel | 604/198 |
| 5,024,616 | 6/1991 | Ogle, II | 604/192 |
| 5,176,656 | 1/1993 | Bayless | 604/198 |
| 5,201,721 | 4/1993 | Lee et al. | 604/198 |
| 5,267,976 | 12/1993 | Guerineau et al. | 604/198 |
| 5,282,793 | 2/1994 | Larson | 604/192 |

FOREIGN PATENT DOCUMENTS

| 0350186 | 1/1990 | European Pat. Off. . |
| 0369619 | 5/1990 | European Pat. Off. . |
| 0405039 | 1/1991 | European Pat. Off. . |
| 0467173A1 | 1/1992 | European Pat. Off. . |
| WO90/07349 | 7/1990 | WIPO . |

OTHER PUBLICATIONS

European Search Report.

Primary Examiner—John D. Yasko
Assistant Examiner—Adam J. Cermak
Attorney, Agent, or Firm—Nixon & Vanderhye

[57] ABSTRACT

Device (10) for retractable needles, which comprises an outer container (20) within which a needle-holder body (14-114) together with a needle (11) can move axially, the outer container (20) containing disarming means (23-123), guide and retention means (17-117-18-19) and spring means (12) cooperating with momentarily inactive diaphragm means (13).

13 Claims, 7 Drawing Sheets

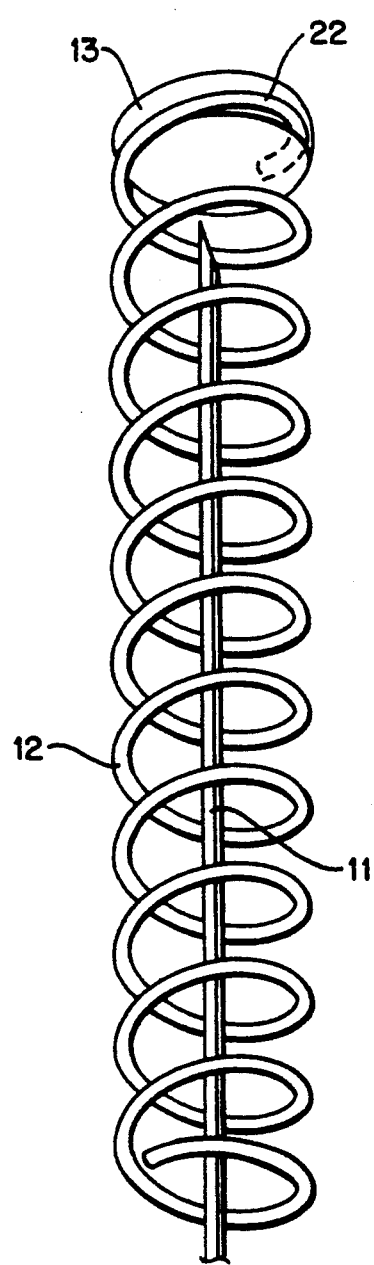
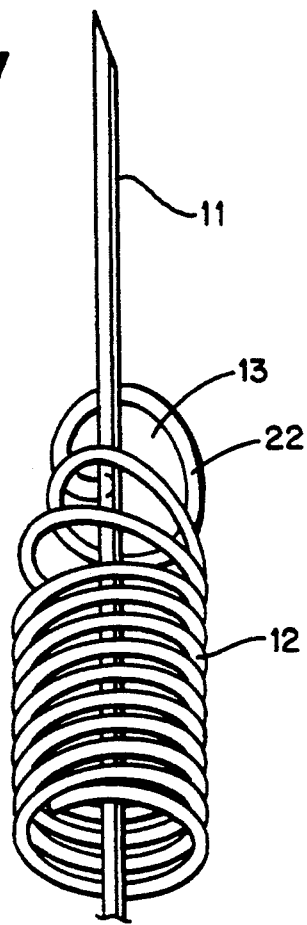
FIG. 6a
FIG. 6b

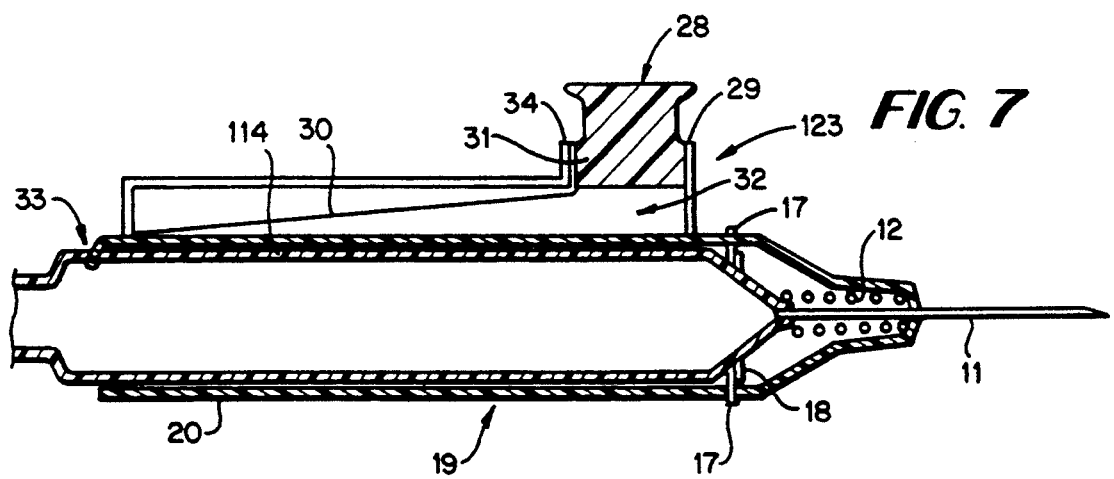
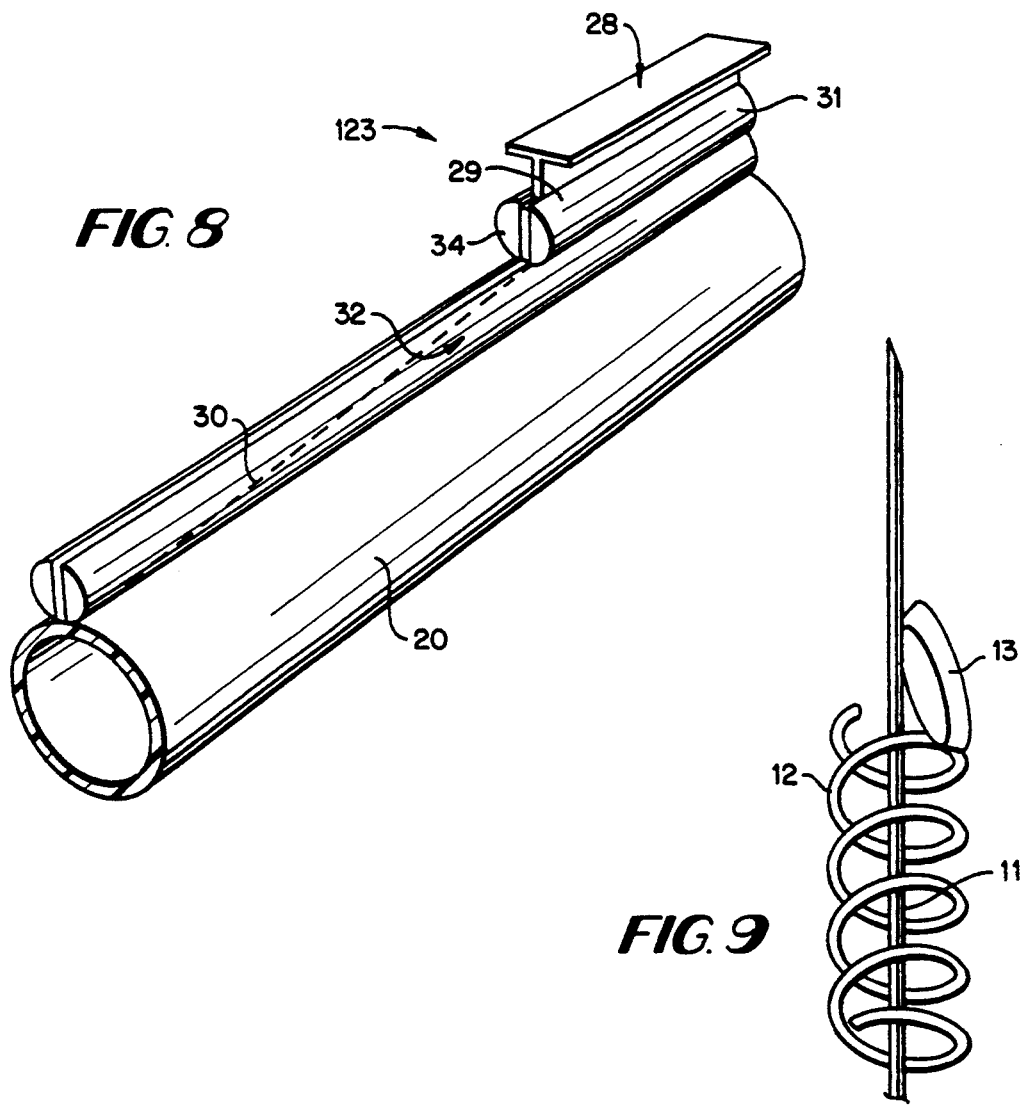

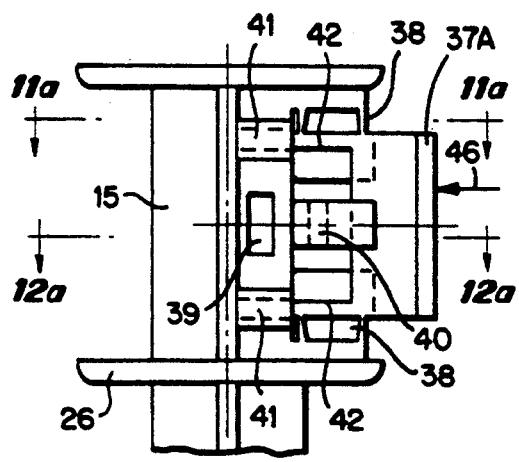
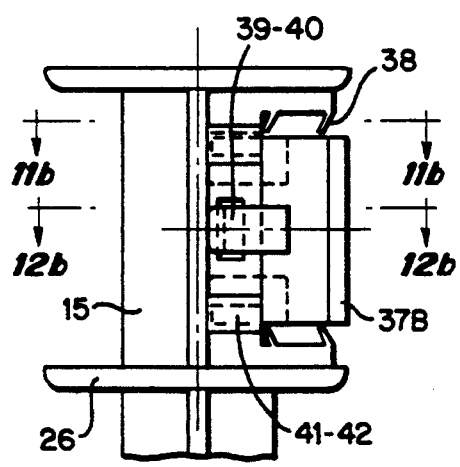
FIG. 10a    FIG. 10b
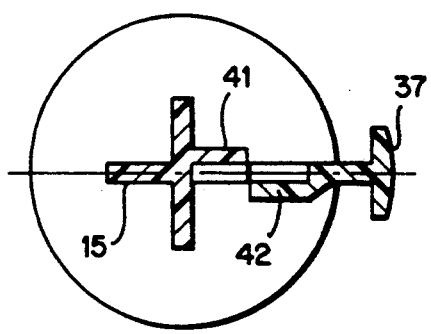
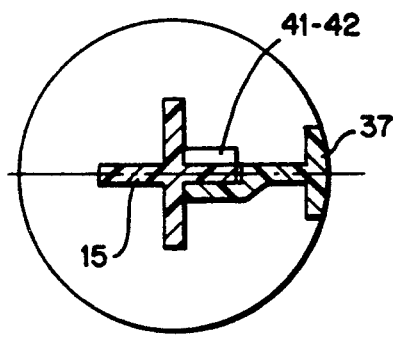
FIG. 11a    FIG. 11b
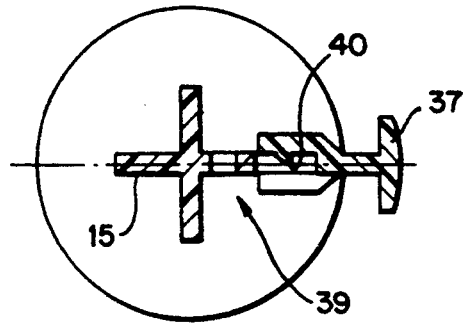
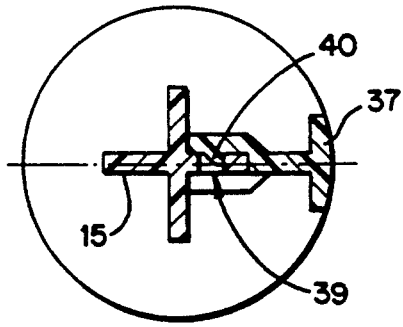
FIG. 12a    FIG. 12b

SINGLE USE RETRACTABLE NEEDLE SYRINGE

BACKGROUND OF THE INVENTION

1. Field of the Invention

This invention concerns a device for single-use retractable needles normally employed to give injections or to take samples on persons and animals with known methods.

The device according to the invention is fitted correctly to single-use syringes and all the needle-holder means employed in transfusions, phleboclysis and like processes.

2. Discussion of Prior Art

The device of this invention is employed mainly in the field of hospitals, doctors' surgeries, household use, etc.

The use of this type of syringe makes possible the prevention of the spread of infectious illnesses which use as their carrier of contagion blood or other liquids easily left in the used needles; in this connection we should bear in mind the methods of the spreading of various types of hepatitis and the acquired immunodeficiency syndrome better known as AIDS.

In this case the spreading of AIDS among drug addicts should mainly be blamed on the re-use of syringes and needles still containing infected substances.

The normal syringes of the "use and throw away" type are generally employed in hospitals, doctors' surgeries, households and, above all, by drug addicts.

The advantages provided by employing single-use syringes which, when once used, cannot be re-used seem to admit of no doubt. The single-use syringes should prevent dangerous transfers of infected substances from one individual to another.

So as to prevent re-use and to ensure their non-offensive nature the single-use syringes generally comprise devices which require the willingness and care of a person who uses these devices.

The single-use syringes of the state of the art contain a device which acts when the plunger is thrust to the end of its travel with a given pressure and is held there.

Other devices require the manual clamping of a retention tooth, while others again require the screwing of protective caps, etc.

Unfortunately in many cases these devices do not work perfectly and therefore allow the syringe to be re-used.

Moreover, certain known devices do not enable the needle to be retracted and are therefore still dangerous.

SUMMARY OF THE INVENTION

The present applicant has designed, tested and embodied the following invention so as to obviate such problems and to enable further advantages to be achieved.

This invention is set forth and characterized in the main claim, while the dependent claims describe variants of the main idea of the solution.

The main aim of this invention is to provide a device for the retraction of single-use needles which comes into action when the plunger of the syringe is substantially at the end of its travel.

At the end of an operation of injection, transfusions or drawing of a sample the device according to the invention enables the needle to withdraw into an appropriate protected seating from which it cannot be extracted.

Thus the only way to come into contact with the needle is to destroy that protected seating. In this way the user is protected from contact with the needle and from involuntary wounds which might be caused by the needle and which might generate pathological results owing to the presence of infected substances on the needle itself.

The invention also has the purpose of producing the device by using normal injection moulding of plastic materials so as to have a very limited effect on the final cost of the syringe itself or of other needle-holder means which employ the device.

The device according to the invention comprises essentially a syringe cooperating with the relative needle-holder, an outer protective container, a disarming spring and a safety diaphragm.

In certain cases, as is known, the needle is fitted directly to the body of the syringe.

A guide and retention element cooperating with the syringe or with the needle-holder enables the syringe to be inserted into the outer protective container during the assembly step and the syringe to slide axially within the outer protective container along a desired, determined segment during the disarming step but does not allow the syringe or needle-holder to be extracted again when once used.

The outer container has a length such that it can contain the whole needle and at least the needle-holder.

According to the invention, when the plunger of the syringe is thrust to the end of its travel, a disarming device is actuated that frees the action of a spring, which makes the syringe slide axially within the outer container and at the same time places between the needle and the relative front outlet of the outer container an interception diaphragm that prevents the emergence of the needle.

The invention takes place in two basic steps. In a first step before the injection the needle emerges from the container so as to be able to carry out its task. In this step the spring is compressed; a part of the compressed spring cooperates with the needle and keeps the diaphragm inactive.

In a second step, when the injection has taken place and the disarming device has been tripped, the needle is wholly positioned within the container and can no longer emerge therefrom owing to the interposition of the diaphragm and the blockage created by the guide and retention element.

According to a variant of the device of the invention, which is especially indicated for the drawing of samples, transfusions, phleboclysis and the like, the employment of a disarming device with controlled manual release by means of an exclusively voluntary act is provided for.

Actuation of the spring, which enables the needle to be wholly retracted within the outer container, is not performed by the disarming device as in the previous case but is carried out voluntarily by hand by pressing an outer surface knob.

This actuation by hand takes place only with a voluntary act and is normally carried out at the end of use of the needle.

This manual voluntary actuation means comprises a catch that cooperates with the syringe or other generic needle-holder body by means of a connecting element.

During the working step the catch is inserted into a suitable retention seating so that it cannot be moved axially.

In this way the syringe too connected to the catch by the connecting element cannot move axially in relation to the outer container.

If the surface knob cooperating with the catch is pressed, the catch is released from the retention seating and is conveyed into an appropriate guide seating.

In this way the syringe is free to move axially and the spring is free to exert a thrust strong enough to bring the needle wholly back within the outer container.

BRIEF DESCRIPTION OF THE DRAWINGS

The attached figures, which are given as a non-restrictive example, show some preferred embodiments of the invention as follows:

FIG. 4 gives a partial and partly cutaway three-dimensional view of the syringe of FIG. 1 in the disarming step;

FIGS. 6a and 6b respectively show the initial and final positioning of the needle, spring and diaphragm;

FIG. 7 shows a section of a variant of the embodiment of FIG. 1;

FIG. 8 is a three-dimensional view of a detail of FIG. 7;

FIG. 9 shows a variant of the needle/spring/diaphragm assembly;

FIGS. 10a and 10b show an obstructing and disarming system for use in carrying the device in an obstructed condition (a) and disarmed condition (b);

FIGS. 11a and 11b show the working of the obstructing system of FIGS. 10 along the section A—A;

FIGS. 12a and 12b show the working of the obstructing system of FIGS. 10 along the section B—B;

DETAILED DISCUSSION OF PREFERRED EMBODIMENTS

The components of a device 10 according to the invention consist advantageously of a moulded plastic material with the exception of a needle 11, spring 12 and possible diaphragm 13, which in this example are made of a suitable material such as steel.

Figure 1:
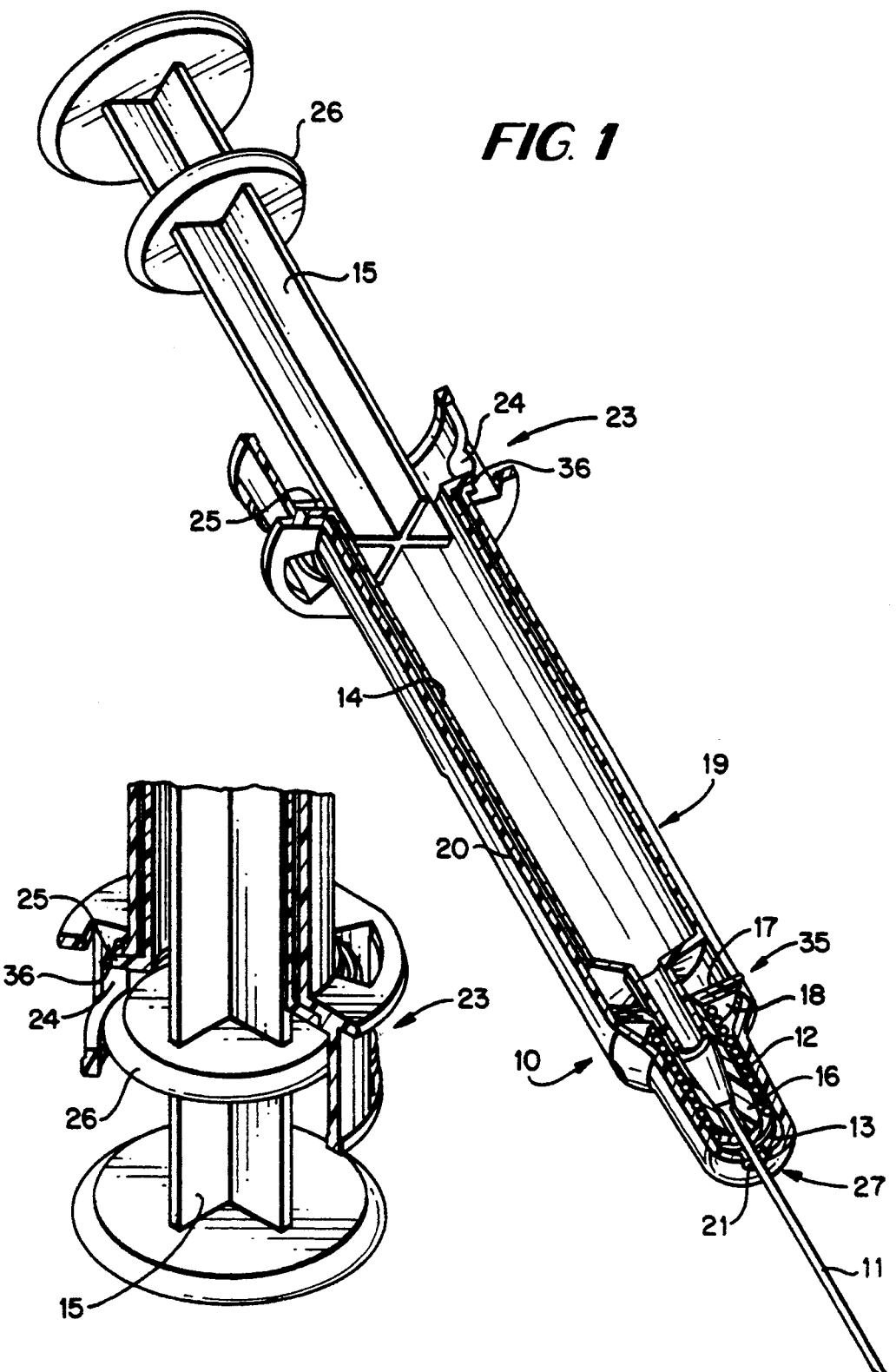
FIG. 1 shows a partly cutaway three-dimensional view of a syringe according to the invention in its first working step.
Figure 2:
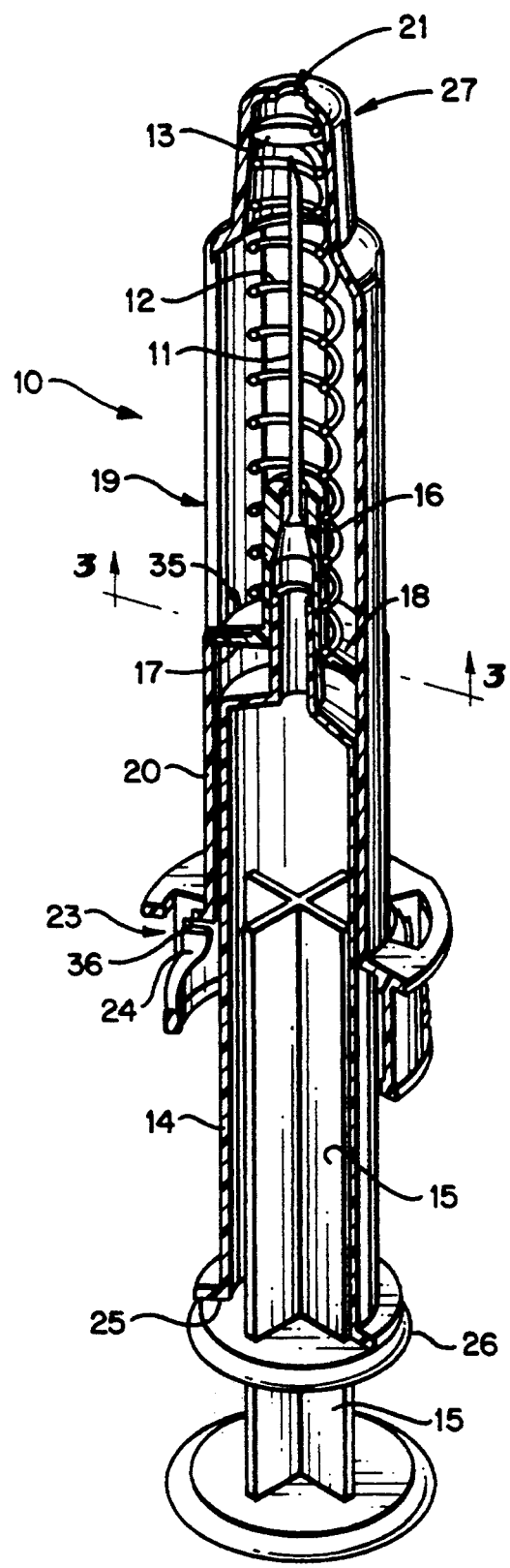
FIG. 2 shows a partly cutaway three-dimensional view of a syringe according to the invention in the second retracted step.
Figure 3:
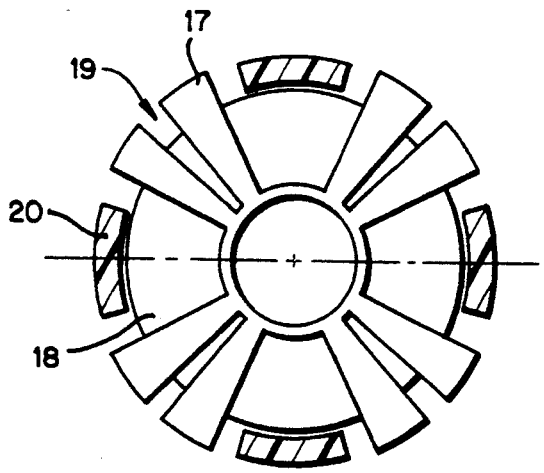
FIG. 3 shows a section A—A of the syringe of FIG. 2.

A body 14 of the syringe and a possible support 16 to hold the needle 11 contain a plunger 15 provided with a normal seal-engagement packing. For the sake of simplicity the plunger 15, which has a known shape, has been cutaway in FIGS. 1, 2 and 4.

The syringe body 14 cooperates externally with an outer protective container 20, which encloses the syringe body 14 fully and has a shape and dimensions such as to enable the needle 11, the needle support 16 and the syringe body 14 to slide in the direction of the axis of the needle 11.

The front end 27 of the outer container 20 is conformed to provide a hole 21 with a diameter slightly greater than that of the needle 11 so that the latter 11 can protrude.

In this case a guide and retention element 35 which includes guide fins 17 and an abutment ring 18 is secured to the needle support 16 rigidly.

According to a variant the guide and retention element 35 could be connected to the syringe body 14 rigidly.

The guide fins 17 cooperate with mating grooves 19 formed in the outer protective container 20.

The grooves 19 have a length such that they halt the travel of the fins 17 when at least the whole needle 11 is completely within the outer container 20.

The special conformation of the guide and retention element 35 enables the needle support 16 to be introduced within the outer container 20 during assembly of the syringe but not to be extracted.

Figure 5A:
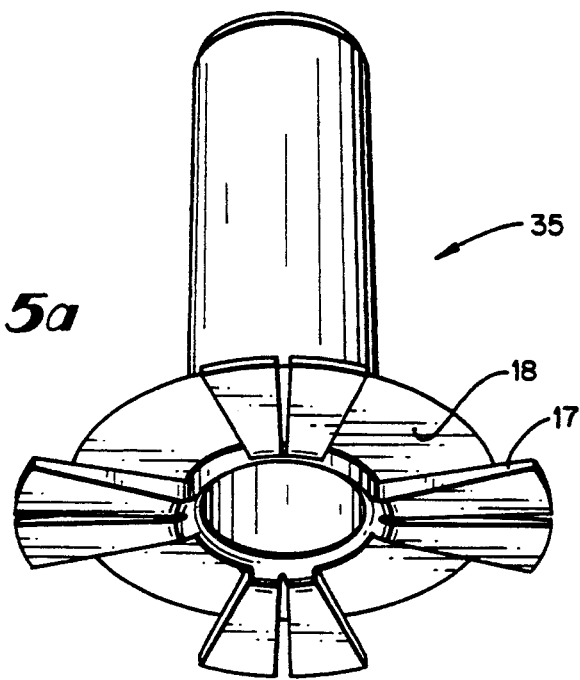
FIGS. 5 show two guide and retention elements.

In fact, in the direction of extraction the inclusion of the abutment ring 18 does not permit the guide fins 17 to be deflected and thus prevents extraction of the needle support 16 from the outer protective container 20 (FIG. 5a).

Figure 5B:
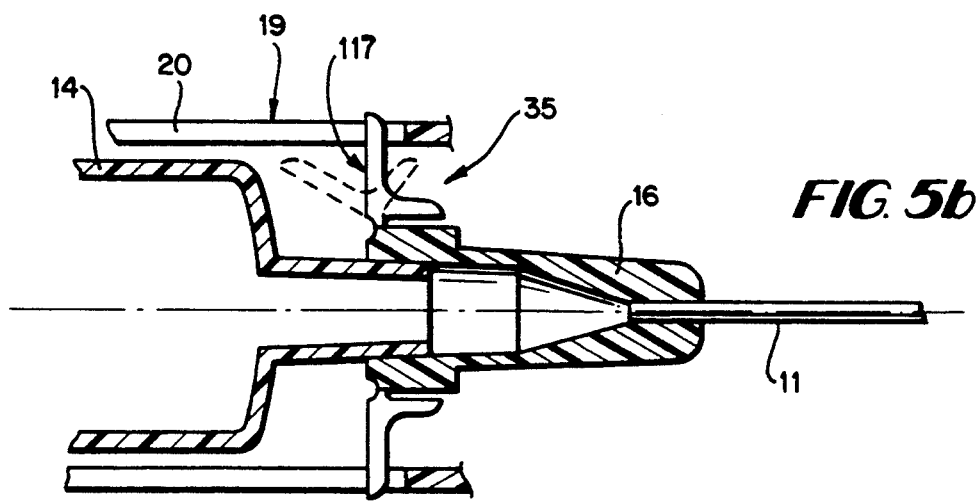

According to the variant of FIG. 5b the grooves 19 cooperate with fins 117 having an L-shaped form and pivoted at the apex of the "L". This conformation has the result that the fins 117 are activated when the syringe body 14 is fitted to the needle support 16.

The fins 117, owing to their conformation, prevent this fitting action being exerted to an excessive extent and thus breaking the needle support 16, since one leg of the fin 117 cooperates with the support 16 itself.

The rear end of the outer container 20 comprises a disarming means 23, which cooperates with a rear flanged clamping edge 25 of the syringe body 14.

In this example the disarming means 23 includes small teeth 24 able to move resiliently in a radial direction and conformed in a manner of a hood. These teeth 24 cooperate with the flanged clamping edge 25 formed on the rear end of the syringe body 14 and prevent, during the first working step, a reciprocal displacement as between the outer container 20 and the syringe body 14.

The teeth 24 comprise ridges 36 which cooperate axially with the flanged clamping edge 25; these ridges 36 prevent any inward sliding of the teeth 24 during the working step.

When the plunger 15 is thrust to the end of its travel, an abutment flange 26 included in the body of the plunger 15 comes into contact with an inner shaped edge of the teeth 24 and displaces the teeth 24 outwards, as shown in FIG. 4.

FIG. 4 shows that the profiles of the teeth 24 and of the abutment flange 26 mate with each other so as to collaborate in an excellent manner. In this way the flanged clamping edge 25 is no longer constrained by the teeth 24 and the syringe body 14 is free to move axially.

According to a variant the teeth 24 can be located on the syringe body 14 instead of on the outer container 20.

In the example shown the needle support 16 cooperates at its front end with the spring 12, which is compressed between the needle support 16 and the front end 27 of the outer container 20.

When the disarming means 23 has been actuated, the spring 12 exerts a thrust strong enough to displace the needle 11 wholly within the outer container 20.

The front end of the spring 12 comprises substantially a suitable diaphragm 13 which cannot be perforated by the needle 11.

The spring 12 (FIG. 6a) in its compressed step has in this case its foremost coil 22 positioned at the side of the needle 11 and acting sideways thereagainst, while the remainder of the spring 12 is coiled about the needle 11.

According to a variant the spring 12 could have a part of its front coils positioned at the side of the needle 11.

According to a further variant the needle 11 passes between the diaphragm 13 and all the coils of the spring 12, and only a part of the foremost coil 22 cooperates with the diaphragm 13.

The purpose of the system is therefore achieved in two basic steps. In a first working step the needle 11 protrudes from the outer container 20 through a hole 21 so as to be able to carry out its function. In this case the spring 12 in this first working step is compressed and the foremost coil 22 bearing the diaphragm 13 is located at the side of the needle 11 and presses thereagainst.

This arrangement is obtained by making the needle 11 emerge from the spring 12 between the diaphragm 13 and the coils or between the coils themselves (FIG. 6a).

In this first working step the teeth 24 of the disarming means 23 in their natural position prevent the syringe body 14 moving axially in relation to the outer container 20.

The second step begins as soon as the abutment flange 26 of the plunger 15 actuates the teeth 24 by overcoming their resilient positioning and displacing them outwards by force, thus releasing the flanged clamping edge 25 of the syringe body 14.

With the disarming means 23 thus tripped, the thrust of the spring 12 causes the needle 11 to disappear wholly within the outer container 20.

When the front end of the needle 11 in its travel of retracting into the outer container 20 passes the front end of the foremost coil 22 of the spring 12, the foremost coil 22 jumps sideways to take up its natural position and in this way draws with it and positions the diaphragm 13 in front of the hole 21 and between the hole 21 and the needle 11 (FIG. 6b).

According to the variant of FIG. 9 the spring 12 during its compressed step rests on the edge of the diaphragm 13 positioned substantially lengthwise to the needle 11.

When the needle 11 has been retracted within the outer container 20, the thrust of the spring 12 and the special shape of the outer container 20 constrain the diaphragm 13 to be positioned in front of the hole 21.

The variant shown in FIGS. 7 and 8 provides a disarming means 123 requiring a voluntary manual release only. This disarming means 123 comprises a catch 29 that cooperates with the needle-holder body 114 by means of a connecting element 30.

The needle-holder body 114 is connected to the suitable connecting element 30 owing to a suitable hole 33 provided in the needle-holder body 114.

In the working step the catch 29 is inserted into a suitable retention seating 31 so that it can move neither axially nor at a right angle to the axis of the outer container 20.

The outer container 20 comprises externally a guide seating 32 with which the retention seating 31 cooperates vertically.

During the working step the catch 29 is prevented from moving at a right angle to the axis of the outer container 20 by the constraint provided by the retention seating 31 and from moving axially by an abutment projection 34, and therefore the axial movement of the needle-holder body 114 too is prevented owing to the presence of the connecting element 30, which in this example is arranged within the guide seating 32.

According to a variant the connecting element 30 during the working step can be located partly or wholly outside the guide seating 32.

When the use of the needle 11 has ended, the disarming means 123 requiring only a voluntary manual release is actuated by pressing a knob 28 cooperating with the catch 29; in this way the catch 29 overcomes the constraint caused by the walls of the retention seating 31 and is displaced into the guide seating 32, in which the catch 29 can move axially freely, and therefore the needle-holder body 114 too can be moved axially within the outer container 20 by the spring 12, which displaces the needle-holder body 114; the needle 11 thus becomes wholly contained within the outer container 20.

Suitable guide fins 17 are formed directly on the needle-holder body 114 and cooperate with suitable mating grooves 19 provided on the outer container 20.

The spring 12 in cooperation with the position of the needle 11 actuates the diaphragm 13.

In FIGS. 10 to 13 the upper part of the plunger 15 comprises an obstruction projection 37-137 above the abutment flange 26. This obstruction projection 37-137 is connected to the upper part of the plunger 15 by connecting bridges 38-45 capable of being broken 38 and bent 45 respectively.

In FIGS. 10 the obstruction projection 37 can move in the direction of the arrow 46 after breakage of the connecting bridges 38; it is guided by the cooperation of mating guides 41-42 and is fixed in its disarming position by anchorage of a resilient tooth 40 in a hole 39.

Figure 13A:
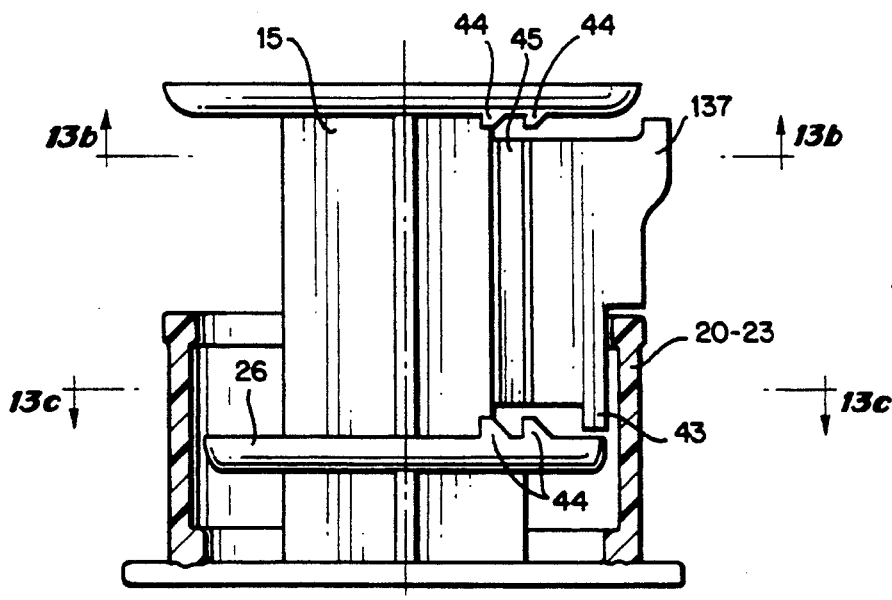
FIGS. 13a, 13b and 13c show a further obstructing system, as a variant of FIGS. 10, in which the sections A—A (b) and B—B (c) are shown.
Figure 13B:
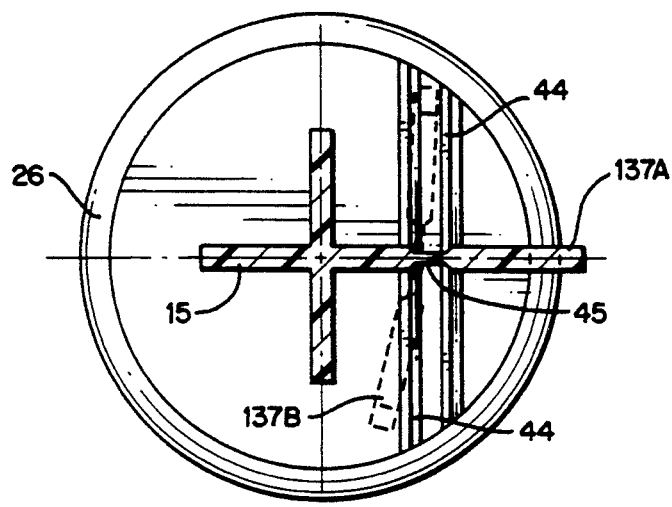
Figure 13C:
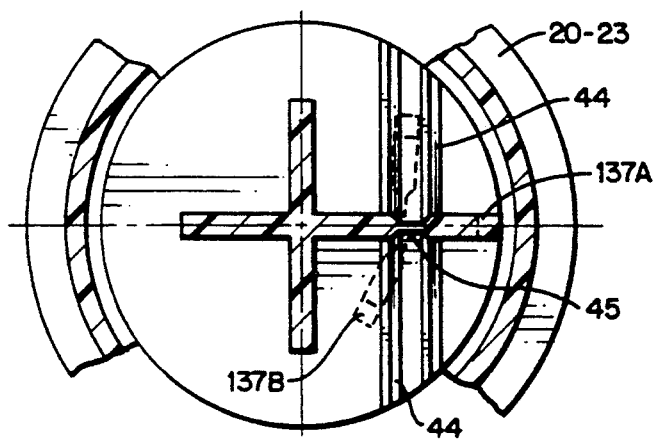

In FIGS. 13 the obstruction projection 137 can move laterally, rotating on the connecting bridge 45, which may be continuous or discontinuous.

The obstruction projection 137 comprises one or more prongs 43, which cooperate with teeth 44 comprised at least on the abutment flange 26. The cooperation of the prong 43 with a tooth 44 obtains a stable disarming position of the obstruction projection 137.

I claim:

1. Device (10) for prevention of multiple use of retractable needles, said device comprising:
   a needle-holder body (14-114), a plunger disposed at least partially within said needle-holder body and a hollow needle (11), where movement of said plunger towards said needle ejects material contained within said needle-holder body through said needle;
   an outer container (20) within which said needle-holder body (14-114) together with said needle (11) can move axially between an active position in which said needle extends at least partially from said container and a disarmed position in which said needle is withdrawn within said container, said container including an aperture through which said needle can be extended;
   means (13) for controllable blocking said aperture, said blocking means comprising an imperforate diaphragm;
   disarming means (23-123) for actuation of said device for prevention of multiple use of retractable needles,
   guide and retention means (17-117-18-19) for centering said needle in said outer container during movement of said needle relative to said outer container towards and through said aperture; and means (12) for biasing said needle-holder body away from said aperture in said container, said biasing means comprising a spring and, cooperating with said diaphragm means (13), responsive to said disarming means, for locating said diaphragm means adjacent said aperture when said needle is withdrawn into said container and for preventing said needle from extending through said aperture.

2. Device (10) as claimed in claim 1 including a clamping flange (25) located on said needle-holder body, in which the disarming means (23) comprises teeth (24) cooperating with said clamping flange (25) to fix the position of said body relative to said container until release of said teeth, an abutment flange (26) disposed on said plunger (15) for releasing said teeth upon termination of movement of said plunger towards said needle.

3. Device (10) as claimed in claim 1, in which the teeth (24) include retaining ridges (36).

4. Device (10) as claimed in claim 1, in which the guide and retention means comprise internal grooves (19) lengthwise on an inner surface of the outer container (20) and fins (17-117) on the needle-holder body (14-114) and cooperating with the grooves (19).

5. Device (10) as claimed in claim 1, in which the guide and retention means comprise internal grooves (19) lengthwise on an inner surface of the outer container (20) and a needle support (16) mounted on said body including fins (17-117) cooperating with the grooves (19).

6. Device (10) as claimed in claim 1, wherein said spring (12) is a coil spring at least partially positioned about the needle (11) and is included axially between the needle-holder body (14-114) and the outer container (20) and, prior to operation of said disarming means, has at least part of a coil (22) positioned at the side of the needle (11) and thrust thereagainst.

7. Device (10) as claimed in claim 6, in which said at least part of a coil (22) cooperates with said diaphragm (13) to bias said diaphragm into a needle blocking position.

8. Device (10) as claimed in claim 6, in which prior to operation of said disarming means, at least a portion of the spring (12) is positioned about the needle (11) and at least one coil is included axially between the needle-holder body (14-114) and the outer container (20) and rests on the edge of the diaphragm (13), which is positioned substantially lengthwise to the needle (11).

9. Device (10) as claimed in claim 6, in which said at least part of a coil (22) bears on the diaphragm (13).

10. Device (10) as claimed in claim 1, in which, when the needle (11) is fully retracted within the outer container (20), the diaphragm (13) is positioned between the needle (11) and said aperture.

11. Device (10) for prevention of multiple use of retractable needles, said device comprising:
a needle-holder body (14-114), a plunger disposed at least partially within said needle-holder body and a hollow needle (11), where movement of said plunger towards said needle ejects material contained within said needle-holder body through said needle;
an outer container (20) within which said needle-holder body (14-114) together with said needle (11) can move axially between an active position in which said needle extends at least partially from said container and a disarmed position in which said needle is withdrawn within said container, said container including an aperture through which said needle can be extended;
means (13) for controllable blocking said aperture, said blocking means comprising an imperforate diaphragm;
disarming means (23-123) for actuation of said device for prevention of multiple use of retractable needles,
guide and retention means (17-117-18-19) for centering said needle in said outer container during movement of said needle relative to said outer container towards and through said aperture; and
means (12) for biasing said needle-holder body away from said aperture in said container, said biasing means comprising a spring and, cooperating with said diaphragm means (13), responsive to said disarming means, for locating said diaphragm means adjacent said aperture when said needle is withdrawn into said container and for preventing said needle from extending through said aperture, further including a means (18) in cooperation with the guide and retention means for preventing the withdrawal of said body from said outer container (20), said preventing means comprising an abutment ring.

12. Device (10) for prevention of multiple use of retractable needles, said device comprising:
a needle-holder body (14-114), a plunger disposed at least partially within said needle-holder body and a hollow needle (11), where movement of said plunger towards said needle ejects material contained within said needle-holder body through said needle;
an outer container (20) within which said needle-holder body (14-114) together with said needle (11) can move axially between an active position in which said needle extends at least partially from said container and a disarmed position in which said needle is withdrawn within said container, said container including an aperture through which said needle can be extended;
means (13) for controllable blocking said aperture, said blocking means comprising an imperforate diaphragm;
disarming means (23-123) for actuation of said device for prevention of multiple use of retractable needles,
guide and retention means (17-117-18-19) for centering said needle in said outer container during movement of said needle relative to said outer container towards and through said aperture; and
means (12) for biasing said needle-holder body away from said aperture in said container, said biasing means comprising a spring and, cooperating with said diaphragm means (13), responsive to said disarming means, for locating said diaphragm means adjacent said aperture when said needle is withdrawn into said container and for preventing said needle from extending through said aperture, in which an upper part of the plunger (15) includes disarming means (37-137) for temporary obstruction of the needle while the needle is being carried.

13. Device (10) for prevention of multiple use of retractable needles, said device comprising:
a needle-holder body (14-114), a plunger disposed at least partially within said needle-holder body and a hollow needle (11), where movement of said plunger towards said needle ejects material contained within said needle-holder body through said needle;

an outer container (20) within which said needle-holder body (14-114) together with said needle (11) can move axially between an active position in which said needle extends at least partially from said container and a disarmed position in which said needle is withdrawn within said container, said container including an aperture through which said needle can be extended;

means (13) for controllable blocking said aperture, said blocking means comprising an imperforate diaphragm;

disarming means (23-123) for actuation of said device for prevention of multiple use of retractable needles, guide and retention means (17-117-18-19) for centering said needle in said outer container during movement of said needle relative to said outer container towards and through said aperture; and means (12) for biasing said needle-holder body away from said aperture in said container, said biasing means comprising a spring and, cooperating with said diaphragm means (13), responsive to said disarming means, for locating said diaphragm means adjacent said aperture when said needle is withdrawn into said container and for preventing said needle from extending through said aperture, in which the disarming means (137) can rock substantially parallel to the axis of the plunger (15) and said plunger includes at least one tooth and said obstructing projection means comprises at least one prong (43) cooperating with said at least one tooth (44) anchored to the plunger (15).

* * * * *